United States Patent
Matsutani et al.

(10) Patent No.: US 7,137,815 B2
(45) Date of Patent: Nov. 21, 2006

(54) ROOT CANAL TREATMENT TOOL AND METHOD FOR MANUFACTURING THE SAME

(75) Inventors: Kanji Matsutani, Tochigi-ken (JP); Kaoru Ohgane, Tochigi-ken (JP); Toshiyuki Takase, Tochigi-ken (JP)

(73) Assignee: Mani, Inc., Shioya-gun (JP)

( * ) Notice: Subject to any disclaimer, the term of this patent is extended or adjusted under 35 U.S.C. 154(b) by 120 days.

(21) Appl. No.: 10/855,492

(22) Filed: May 28, 2004

(65) Prior Publication Data

US 2005/0003325 A1 Jan. 6, 2005

(30) Foreign Application Priority Data

May 29, 2003 (JP) ............................ 2003-152564

(51) Int. Cl.
*A61C 5/02* (2006.01)
(52) U.S. Cl. .................................... 433/102
(58) Field of Classification Search ................ 433/102, 433/81, 224
See application file for complete search history.

(56) References Cited

U.S. PATENT DOCUMENTS

| | | | | |
|---|---|---|---|---|
| 5,775,902 A | * | 7/1998 | Matsutani et al. | 433/102 |
| 5,897,316 A | * | 4/1999 | Buchanan | 433/102 |
| 5,984,679 A | * | 11/1999 | Farzin-Nia et al. | 433/102 |
| 6,149,501 A | * | 11/2000 | Farzin-Nia et al. | 451/48 |
| 6,299,445 B1 | * | 10/2001 | Garman | 433/102 |
| 6,315,558 B1 | * | 11/2001 | Farzin-Nia et al. | 433/102 |
| 6,375,458 B1 | * | 4/2002 | Moorleghem et al. | 433/2 |

FOREIGN PATENT DOCUMENTS

EP  0 684 019 A1  4/1995

* cited by examiner

Primary Examiner—John J. Wilson
Assistant Examiner—Meoghan E. MacPherson
(74) Attorney, Agent, or Firm—Townsend & Banta

(57) ABSTRACT

The present invention relates to a root canal treatment tool that is formed in a shape of a rod and has a work portion formed in a predetermined length from a tip and a shank formed in a manner continuous with the work portion. The work portion has a shape memory characteristic in a range of a predetermined length from the tip and a superelastic characteristic in a remaining portion.

2 Claims, 4 Drawing Sheets

(a)

(b)

(c)

ROOT CANAL TREATMENT TOOL AND METHOD FOR MANUFACTURING THE SAME

FIELD OF THE INVENTION

The present invention relates to a root canal treatment tool for dental treatment, and a method for manufacturing this root canal treatment tool.

BACKGROUND OF THE INVENTION

Various tools for treating the root canal of a tooth exist, including, for example, a reamer and a file that cut and form a root canal, a compactor, a filler, a spreader, and a plugger that fill the root canal with thermoplastic resin; a cleanser that removes remainders in the root canal; and a broach that fills the root canal with cotton. The above-described reamer and file is constructed of a slender tapered rod having a work portion provided with a cutting blade or piercing protrusion appropriate for a treatment object or a member having a work portion formed by forming a tapered rod in a spiral shape. Moreover, the tools described above comprised of a handle or a grip integrated with the end of the member, so that the tool may be gripped or operated by a dentist, or is constructed of a shank, so that it may be gripped by a chuck of a hand piece or the like, or is directly operated by the dentist.

The root canal is excessively thin and has a variety of shapes and sizes, and varies between persons. For this reason, tools of many different sizes are needed, even for the same kind of root canal treatment tools. For example, in the case of cutting and forming a root canal by use of a reamer, the reamer is required to be deformed along the shape of the root canal, that is, to have appropriate elasticity so that it should not hurt the surrounding root canal. Japanese Patent No. 3375765 discloses a root canal treatment tool having extremely high elasticity and a shape restoration property as described above. This technology relates to a root canal treatment tool having a work portion formed and manufactured by applying a removing work to a rod-shaped raw material that is subjected to shape memory heat treatment, and has a superelastic characteristic while holding it under a memory treatment temperature.

In the above-mentioned root canal treatment tool, the rod having the work portion formed thereon is flexibly deformed in response to an external force applied thereto, and is quickly restored to an original shape when the external force is removed. For this reason, this tool can conform well to the shape of the root canal, and form the root canal with high accuracy.

In the root canal treatment tool relating to the Japanese Patent No. 3375765, the work portion has the superelastic characteristic uniformly along the whole length and, hence, when the work portion is bent, a tip portion of a free end also has an action of returning to an original shape. Accordingly, when the tip portion is inserted into the root canal for the treatment of the root canal and is bent, a repulsive force is generated to act on the wall of the root canal. Thus, there is an undesirable possibility that, in the vicinity of a root sharp mouth (tip of the work portion), the work portion might cut the outside of a bent portion of the root canal more heavily, and might cut the inside in the center of the bent portion more heavily, so as to penetrate the root canal.

Moreover, since the root canal treatment tool is rotated in a state where the work portion is bent almost along the whole length from the tip at the time of forming the root canal, a repeated bending stress is applied to the work portion. This increases the possibility of breaking a slender tip portion of the work portion. For this reason, although the root canal treatment tool relating to the Japanese Patent No. 3375765 has sufficiently high durability as compared with a root canal treatment tool made of stainless steel, it lacks sufficient durability.

SUMMARY OF THE INVENTION

The object of the present invention is to provide a root canal treatment tool that, unlike the conventional tool, is not apt to go out of the root canal and that is enhanced in durability by weakening the action of returning to an original shape of the tip portion of the work portion, and a method for manufacturing the root canal treatment tool.

In order to solve the above problems, a root canal treatment tool according to the present invention is provided that is formed in the shape of a rod, has a work portion formed in a predetermined length from a tip and a shank formed in a manner continuous with the work portion, and is such that the work portion has a shape memory characteristic in the range of a predetermined length from the tip and a superelastic characteristic in a remaining portion.

In the root canal treatment tool of the present invention, the work portion has the shape memory characteristic in the range of a predetermined length from the tip, and the superelastic characteristic in the remaining portion. For this reason, in a state where the tip does not recover a memory shape, even when a small force is applied to the tip from the outside, it is easily deformed in response to this force. That is, the tip having the shape memory characteristic can be freely deformed by a small force as compared with the other portion having the superelastic characteristic.

Therefore, the tip of the work portion loses an action of returning to an original shape and hence conforms well to the shape of the root canal, and does not deviate from the root canal at the time of forming the root canal. Furthermore, the tip portion becomes soft to improve durability when the work portion is rotated at the time of forming the root canal.

Further, a method for manufacturing a root canal treatment tool according to the present invention is provided, comprising:

subjecting a portion of a wire provided with a superelastic characteristic by a memory heat treatment to a working of removing metal;

subjecting a portion of the portion of a wire subjected to the working of removing metal to heat treatment to provide the portion with a shape memory characteristic, or a portion of the wire provided with the superelastic characteristic by the memory heat treatment is again subjected to heat treatment to provide the portion with the shape memory characteristic; and then subjecting the portion having the shape memory characteristic and the portion that is continuous with the portion having the shape memory characteristic and that has the superelastic characteristic to the working of removing metal.

According to the above method for manufacturing a root canal treatment tool, the wire provided with the superelastic characteristic is previously subjected to the working of removing metal, thereby being formed into the shape of an objective root canal treatment tool, and then the tip portion of the work portion is again subjected to heat treatment. In this manner, it is possible to manufacture the root canal treatment tool having the work portion that is provided with the shape memory characteristic in the tip and the superelastic characteristic in the remaining portion. Moreover, a portion of the wire provided with the superelastic characteristic is previously again subjected to heat treatment, thereby being provided with the shape memory characteristic, and then is subjected to the working of removing metal, thereby being formed into the shape of the objective root canal treatment tool. In this manner, it is possible to manufacture the root canal treatment tool of the present invention having the work portion that is provided with the shape memory characteristic in the tip and the superelastic characteristic in the remaining portion.

DETAILED DESCRIPTION OF THE INVENTION

Figure 1:
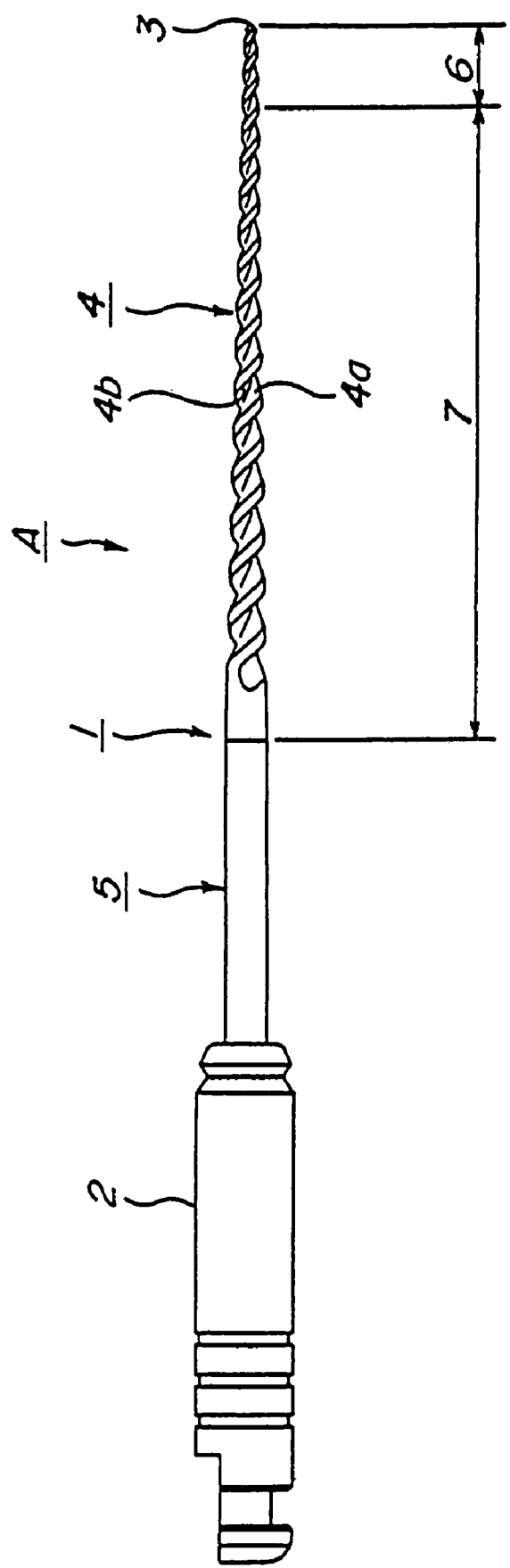
FIG. 1 is a side view of a the root canal treatment tool of the present invention.

The preferred embodiment of a root canal treatment tool according to the invention will be described below with reference to drawings and the preferred method for manufacturing the same.

The root canal treatment tool according to the present invention is a tool for treating a root canal, and includes all tools formed by use of a rod-shaped material. In this root canal treatment tool, a work portion having a shape capable of performing an objective treatment most reasonably is formed at one end portion, and an operation portion operated by a dentist is formed at an opposite end portion. When the dentist directly operates the tool, this operation portion is formed into a handle, and when a tool such as a hand piece is used, the operation portion is provided with a grip formed in a shape suitable for the structure of the grip of the tool.

The shape of a reamer A will be described as an example of the root canal treatment tool with reference to FIG. 1. The reamer A is a tool for cutting a wall of the root canal, and is constructed of a needle portion 1 and a grip 2. In the needle portion 1, a tapered work portion 4 extending a predetermined length from a tip 3 is formed, and a straight shank 5 is formed in a manner continuous with the work portion 4.

The work portion 4 is provided in various cross sections according to the kind of reamer, such as rectangle, triangle, or square, so as to perform its unique function.

In the reamer in this embodiment, a rectangular cross section is formed in the shape of a spiral along the work portion 4, to form a groove 4a and a cutting edge 4b along the groove 4a. The shank 5 has a function of being mounted in the grip 2. The grip 2, as shown in FIG. 1, is formed so as to be gripped in the chuck of a handle piece, or so as to be gripped and operated by a dentist, thereby being formed in the shape and of material corresponding to the respective functions.

For example, the grip 2 is made of metal such as stainless steel or the like, and has a shank 5 inserted into a hole made in its center and fixed thereto with adhesive. Moreover, in the case of forming a grip to be gripped and operated by hand by the dentist, the grip may be also molded by the injection molding of synthetic resin, so as to have the shank 5 inserted therein, thereby being integrated with and fixed to the shank 5.

The needle portion 1 is made of metal having a shape memory characteristic, for example, nickel-titanium (Ni—Ti) alloy, and is formed of a wire having a diameter corresponding to the diameter of the needle portion 1 constructing the reamer A. A portion extending a predetermined length from the tip 3 of the work portion 4 is formed as a shape memory portion 6 having the shape memory characteristic, and a portion on the shank 5 side nearer to the shape memory portion 6 in the work portion 4 is formed as a superelastic portion 7 having a superelastic characteristic.

The shape memory portion 6 in the needle portion 1 is provided with such a characteristic by performing heat treatment on the Ni—Ti alloy, so as to cause the Ni—Ti alloy to not recover a memory shape in the range of a room temperature or a body temperature. When the shape memory portion 6 reaches a shape recovery temperature, it recovers a previously stored shape, and exerts high strength. However, when an external force is applied to the shape memory portion 6 in a state where it does not reach the shape recovery temperature, the shape memory portion 6 is easily deformed in shape in response to the external force applied thereto. Therefore, the shape memory portion 6 does not exhibit the characteristic of returning to its original shape, but can be deformed in a preferable shape.

For this reason, the dentist can bend (pre-curve) the shape memory portion 6 in correspondence with the shape of root canal or the root sharp mouth of a patient at the time of treatment. This pre-curving of the shape memory portion 6 enables the tip 3 and the shape memory portion 6 to follow the root canal with high fidelity at the time of inserting the tip 3 into the root canal and performing treatment on the root canal. Then, when the dentist takes the root canal treatment tool out of the root canal after finishing the treatment, he can deform it to the original shape by applying a force to the shape memory portion 6, or can recover its memory shape by increasing its temperature to the shape recovery temperature.

As described above, the shape memory portion 6 that does not recover the memory shape has high flexibility and a high fatigue resistance characteristic. For this reason, when the work portion 4 is bent and rotated in a state where the tip 3 is inserted into the root canal, a fatigue fracture time can be elongated as compared with a tool whose work portion has a superelastic characteristic along the whole length.

The superelastic portion 7 memorizes the shape of a straight needle and keeps a state where a memory shape is formed in the shape of the straight needle in the range of room temperature. This superelastic portion 7 has extremely high flexibility and high restorability. That is, the superelastic portion 7 is easily deformed (bent) in response to an external force applied thereto, but is easily restored to an original shape when the application of the external force is removed.

In particular, because the work portion 4 is formed in the shape of a taper, when the work portion 4 is bent with a fulcrum at the tip 3, the shank 5 is kept nearly in a straight line, and the superelastic portion 7 is bent into the shape of an arc having a small curvature on the shank 5 side and is heavily bent into the shape of an arc that increases a curvature as its portion is closer to the shape memory portion 6 side and the shape memory portion 6 is further heavily bent. That is, the work portion 4 is not uniformly bent, but rather is bent in response to the taper. When the bending of the work portion 4 is released, the superelastic portion 7 is restored to the original shape (in the shape of a straight needle), and the shape memory portion 6 keeps a bent shape.

The length of the shape memory portion 6 in the work portion 4 is not limited to a special value. According to the tests performed by the present inventors, in the work portion having a superelastic characteristic along the whole length, in many cases, the work portion was broken in a portion at 2 mm to 3 mm from the tip. For this reason, the length of the shape memory portion 6 in the work portion 4 needs to be at least 2 mm from the tip 3. Although the maximum length is not limited to a special length, the maximum length is about ¾ of the whole length of the work portion 4. Moreover, when the length of the work portion 6 is 16 mm, the particularly preferable length range of the shape memory portion 6 is from about 3 mm to 6 mm from the tip 3, and more preferably about 3 mm or 4 mm.

If the length of the shape memory portion 6 is smaller than 2 mm, durability is not substantially different as compared with a reamer having a superelastic characteristic along the whole length of the work portion. Moreover, if the length of the shape memory portion 6 is larger than ¾ of the work portion, at the time of inserting the tip 3 into the root canal and rotating it, a problem may occur in that the position of a rotational axis is not fixed, but is made eccentric to make it difficult to cut the root canal well.

Although the memory shape in the shape memory portion 6 is not limited to a special one, the shape memory portion 6 is preferably formed in the shape of a straight needle as an extension of the superelastic portion 7. Moreover, it is preferable that the shape recovery temperature of the shape memory portion 6 is sufficiently higher than room temperature and body temperature. That is, when the shape recovery temperature is as high as the body temperature, there might be a possibility that while the root canal is treated, the memory shape is recovered, thereby presenting the same problem encountered when the work portion 4 has the superelastic characteristic along the whole length. Hence, it is necessary that the shape recovery temperature of the shape memory portion 6 is sufficiently higher than the room temperature or the body temperature. Such a temperature includes a processing temperature at the time of autoclave sterilization but, needless to say, it is not intended to limit the shape recovery temperature to this temperature.

In the case of using the above reamer A, as illustrated in FIG. 1, it is possible to cut the wall of the root canal and to form the root canal in the following manner: a dentist makes the chuck of a hand piece (not shown) grip the grip 2, holds the hand piece, bends the shape memory portion 6 formed on the tip 3 side of the work portion 4 in correspondence to the shape of the patient's root canal, and then inserts the tip 3 into the root canal and moves it in the axial direction while rotating it in a direction of the cutting edge 4b.

Incidentally, because the reamer A as a root canal treatment tool is taken as an example in this embodiment, the cutting edge 4b is formed on the reamer A. However, all of the root canal treatment tools do not necessarily have the cutting edge 4b formed on their work portions 4 but some of them have a needle-shaped protrusion or a tapered coil formed on the work portions. Even in such a root canal treatment tool, by forming the shape memory portion 6 within a predetermined range from the tip 3 of the work portion 4, and by forming the remaining portion of the superelastic portion 7, it is possible to prevent the tool from being withdrawn from the root canal and to improve durability.

Next, a first manufacturing method for manufacturing the reamer A will be described with reference to FIGS. 2A, 2B, and 2C. The first manufacturing method is a method by which a raw material previously provided with a superelastic characteristic is subjected to a working of removing metal to form a work portion, and by which the tip side of the work portion is again subjected to a heat treatment to provide the tip side with a shape memory characteristic.

Figure 2:
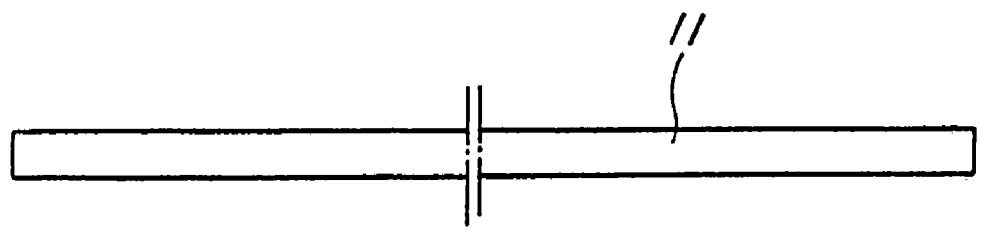
FIG. 2A is an illustration of a side view of Ni—Ti wire used to form the rod-shaped raw material used to manufacture the root canal treatment tool of the present invention.
FIG. 2B is a side view of the needle portion 1 of the root canal treatment tool shown in FIG. 1, illustrating the construction of the tapered work portion after working of the raw material shown in FIG. 2 according to the method of the present invention.
FIG. 2C is a side view of the needle portion 1 of the root canal treatment tool shown in FIG. 1, illustrating the superelastic portion 7 and shape memory portion 6 formed after heat treatment of the needle portion 1 according to the method of the present invention.
Figure 2:
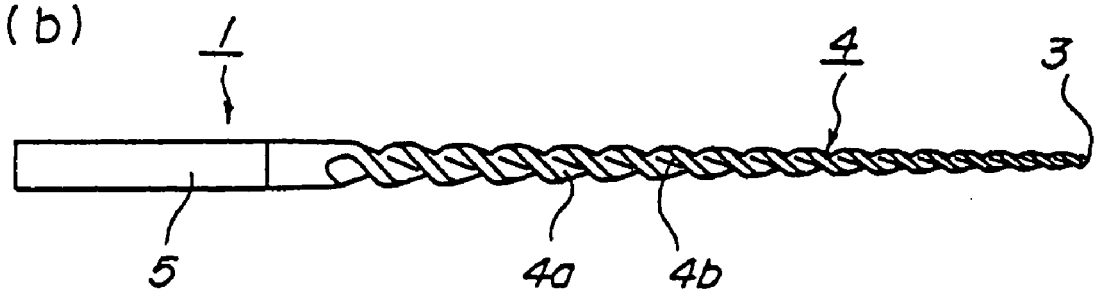
Figure 2:
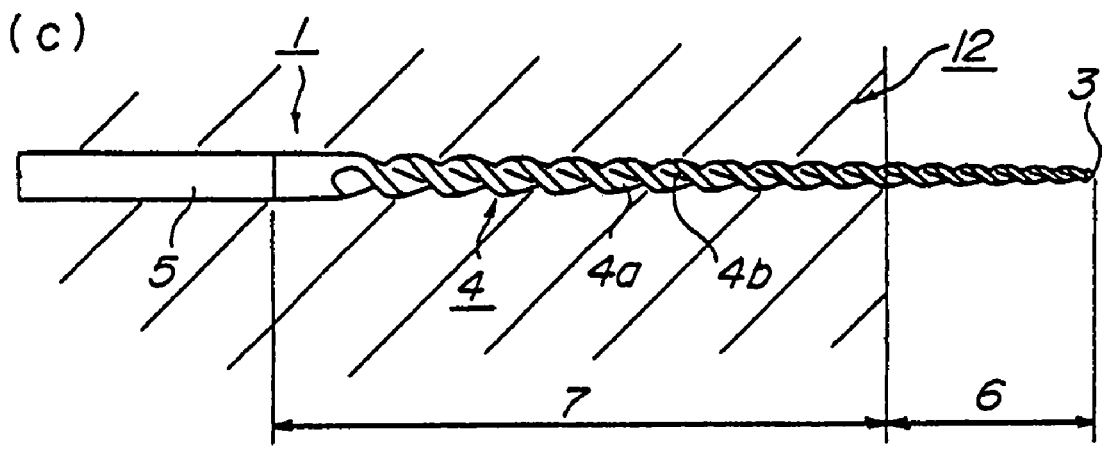

As shown in FIG. 2A, a wire made of a Ni—Ti alloy previously provided with a superelastic characteristic and having a diameter corresponding to the size of the objective reamer A is cut in correspondence with the length of the reamer A to form a rod-shaped raw material 11.

As shown in FIG. 2B, the raw material 11 is worked into the shape of a taper, is worked to form the groove 4a and the cutting edge 4b, and is further worked to form the tip 3, whereby the work portion 4 and the shank 5 are formed. In this manner, the needle portion 1 is formed. At the time of working the raw material 11, the raw material 11 can not be plastically worked because it has a superelastic characteristic. For this reason, the workings of tapering the raw material 11 and forming the groove 4a and the cutting edge 4b are performed by a working of removing metal, including a cutting working. The work portion 4 formed in this manner has the superelastic characteristic along the whole length thereof.

Next, the shape memory portion 6 is formed in a range of a predetermined length from the tip 3 of the work portion 4. This process, as shown in FIG. 2C, is performed as follows: portions other than a portion corresponding to the shape memory portion 6 in the needle portion 1 are cooled by a cooling agent 12, and the shape memory portion 6 is heated on the basis of heat treatment conditions set for the raw material 11 in a state where the shape memory portion 6 is kept in an objective shape (in the shape of a straight needle in this embodiment). Any one of the following methods can be selected as a specific example of a method for forming the shape memory portion 6.

Figure 4:
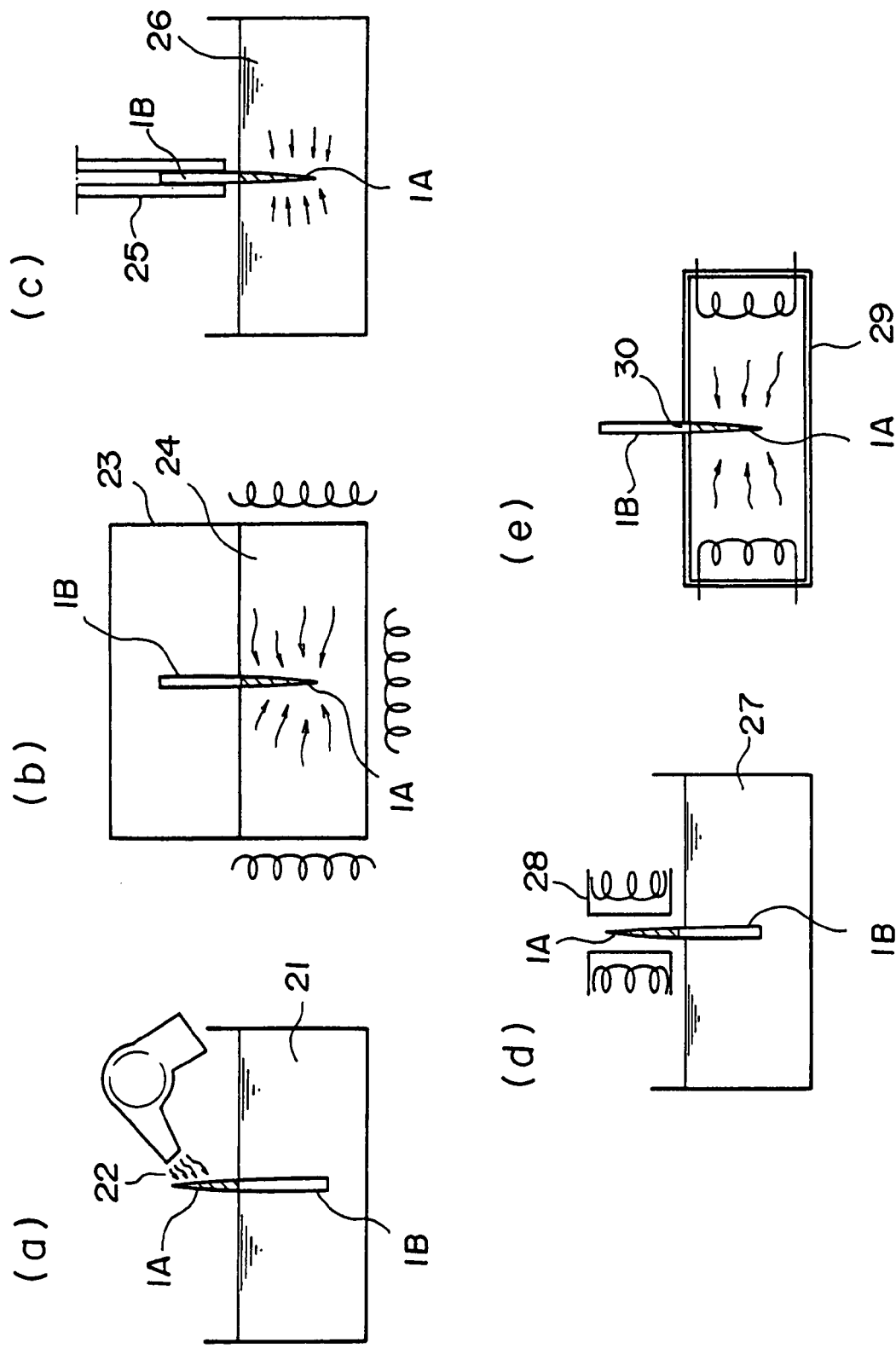
FIG. 4(a) is an illustration of a partial heating method of the work portion by hot air of the present invention.
FIG. 4(b) is an illustration of a partial heating method of the work portion by a furnace of the present invention.
FIG. 4(c) is an illustration of a partial heating method of the work portion by liquid of the present invention.
FIG. 4(d) is an illustration of a partial heating method of the work portion by solid of the present invention.
FIG. 4(e) is an illustration of a partial heating method of the work portion by heating pod of the present invention.

(A) Partial heating method by hot air (see FIG. 4A)

A portion 1B not to be heat-treated is partially dipped in water 21 as a cooling agent so as to prevent a temperature increase or is blown by cool air and, at the same time, a portion 1A to be heat-treated is blown by hot air 22, thereby being partially heated.

(B) Partial heating method by a furnace (see FIG. 4B)

A furnace 23 is partitioned into two layers and a portion 1A to be heat-treated is partitioned by heat insulating material 24 so as to prevent a portion 1B not to be heat-treated from being increased in temperature and is heated in the furnace 23. Here, if a portion 1A can be surely insulated from heat, the furnace 23 is not required to be partitioned.

(C) Partial heating method by liquid (see FIG. 4C)

A portion 1B not to be heat-treated is held by a clip 25 provided with a cooling function, and a portion 1A to be heat-treated is dipped in liquid in a salt bath 26 at high temperatures, thereby being heated.

(D) Partial heating method by solid (see FIG. 4D)

A portion 1B not to be heat-treated is dipped in a cooling agent 27, such as water, to prevent a temperature increase, and a portion 1A to be heat-treated is brought into contact with or close to a heating body 28 at high temperatures, thereby being heated.

(E) Partial heating method by heating pod (see FIG. 4E)

A small hole 30 through which a work piece (wire) can be inserted is made in a heating pod 29, and only a portion 1A to be heat-treated is inserted into this small hole 30, thereby being partially heated. Here, a portion not to be inserted into the heating pod 29 (portion not to be heat-treated) 1B may be blown by cool air, thereby being actively cooled.

The cooling agent 12 for cooling a portion other than the shape memory portion 6 at the time of heat-treating the shape memory portion 6 is not limited to a special one but, for example, water can be used.

The shank 5 of the needle portion 1 provided with the shape memory portion 6 in the range of a predetermined length from the tip 3 is inserted into and bonded to a grip (not shown), whereby the objective reamer A can be manufactured.

A second manufacturing method according to the present invention is a method by which the raw material 11 shown in FIG. 2A is heat-treated in the range of a predetermined length from a tip on one side at the step of forming the raw material 11 to provide it with the shape memory characteristic, and by which the raw material 11 is then subjected to a working including the removal of metal to form the work portion 4 having the groove 4a and the cutting edge 4b to manufacture an objective reamer A.

According to the above second manufacturing method, at the step of the raw material 11, a portion having the shape memory characteristic and a portion having the superelastic characteristic are formed, and then the raw material 11 is subjected to the working of removing metal to form the work portion 4. Therefore, in the shape memory portion 6, the shape of a straight needle is memorized, and groove 4a and the cutting edge 4b are formed continuous with the superelastic portion 7 formed thereon.

As described above, the raw material 11 having the portion corresponding to the shape memory portion and the portion corresponding to the superelastic portion is subjected to the working, including the removal of metal, to form the needle portion 1, including the work portion 4 and the shank 5. Then, the shank 5 is inserted into and bonded to the grip (not shown), whereby the objective reamer A can be manufactured.

The present inventors manufactured five samples (conventional samples), each of which was a No. 30 reamer formed of a raw material of about 1.0 mm in diameter and having a tip portion of about 0.3 mm in diameter, a taper of 4/100, a rectangular cross section, a needle portion protruding from the grip 2 and having a length of about 25 mm, and a work portion having a length of about 15 mm, wherein the work portion had a superelastic characteristic along the whole length thereof; five samples (first method samples) each of which had the shape memory portion 6 formed in the range of about 4 mm from the tip 3 and had the superelastic portion 7 formed in the remaining work portion 4 by the first manufacturing method; and five samples (second method samples) each of which had the shape memory portion 6 formed in the range of about 4 mm from the tip 3 and had the superelastic portion 7 formed in the remaining work portion 4 by the second manufacturing method, and then conducted tests of bending tests and fatigue fracture tests.

Incidentally, the heat treatment for forming the shape memory portion 6 in the work portion 4 is performed on the thin rod within a limited range, and hence a boundary is not clearly produced between the shape memory 6 and the superelastic portion 7. For this reason, it is difficult to express the range of length from the tip 3 of the shape memory portion 6 by an exact numerical value, but there is no other choice but to express that the shape memory portion 6 is formed in the range of about 4 mm.

In the bending test, the work portion 4 was gripped at a position of about 3 mm from the tip 3, and torque when the work portion 4 was bent about 45 degrees in this state was measured. As a result, the average value of the conventional samples was about 51 gf-cm, the average value of the first method samples was about 43 gf-cm, and the average value of the second method samples was about 45 gf-cm.

From the above measurement results, it can be said that the reamer A having the shape memory portion 6 in the range of about 4 mm from the tip 3 of the work portion 4 can be bent by smaller torque, as compared with a reamer having the superelastic characteristic along the whole length. That is, the reamer A according to the present invention has higher flexibility in the range of about 4 mm from the tip 3, as compared with the conventional reamer.

Therefore, even if the shape memory portion 6 is forcibly bent, and then the bending force is released, the bent shape of the shape memory portion 6 can be maintained. For this reason, at the time of treating the root canal, it is possible to bend the shape memory portion 6 previously according to the shape of the patient's root canal, to insert the tip 3 into the root canal, and to perform treatment with this maintained bent shape. That is, it is possible to make the shape memory portion 6 conform to the shape of the root canal before and during treatment.

Moreover, even when treatment for the root canal progresses, and where the tip 3 reaches the root sharp mouth, because the shape memory portion 6 is easily bent, the shape memory portion 6 does not apply a repulsive force to the wall of the root canal. This prevents the shape memory portion 6 from cutting the wall of the root canal more heavily near the root sharp mouth, and in the center of curve and deviating from the root canal.

Figure 3:
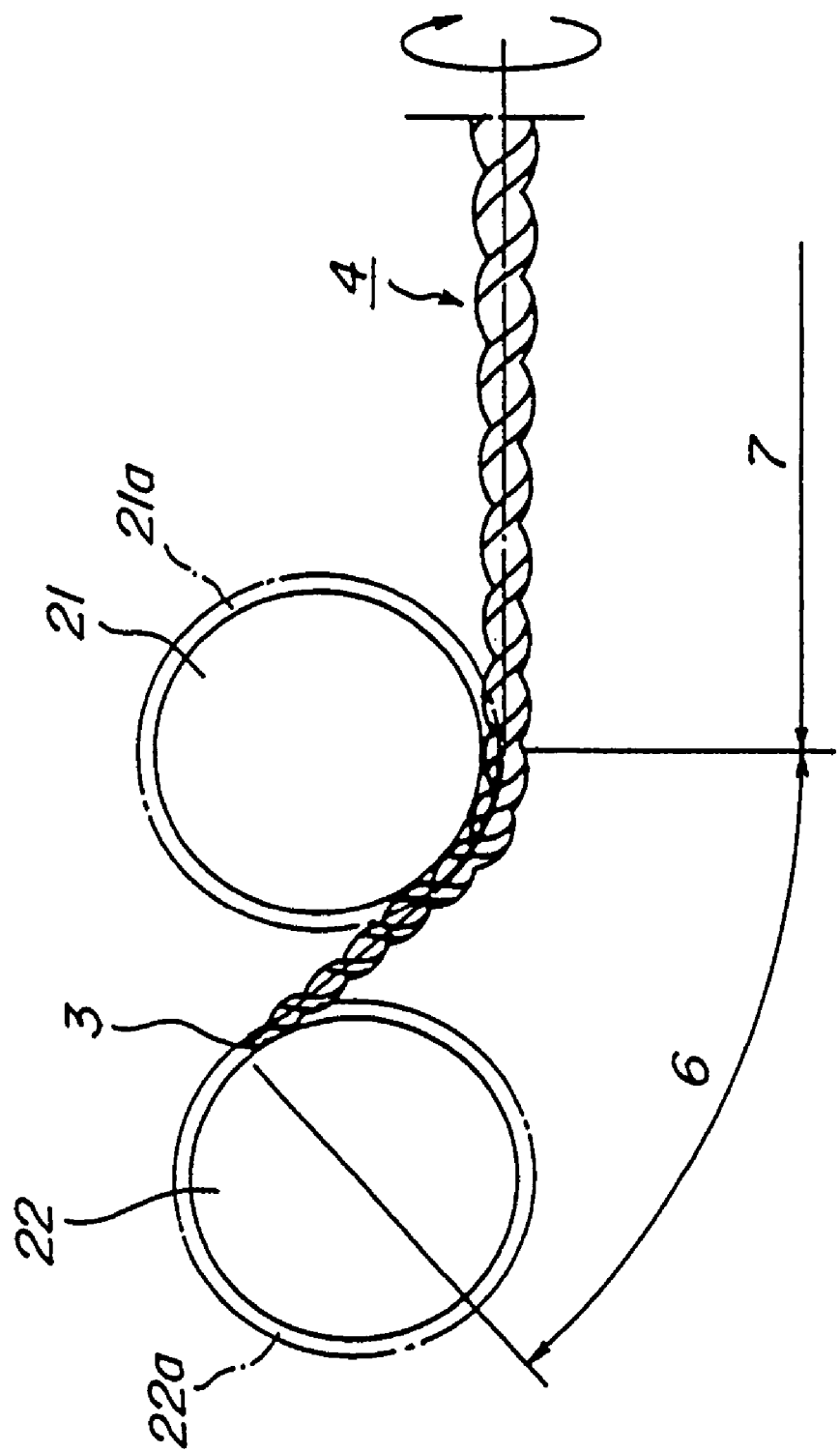
FIG. 3 is a partial schematic view illustrating the application of a fatigue fracture test on the tip portion of a root canal treatment tool according to the present invention.

The fatigue fracture tests were conducted by use of an apparatus shown in FIG. 3. That is, by use of the apparatus having a pair of pins 21, 22 having grooves 21a, 22a capable of receiving the tip 3 side of the work portion 4, the work portion 4 was set such that a position of 4 mm from the tip 3 of the work portion 4 corresponded to the center of one pin 21 and that the tip 3 was inserted into the groove 22a of the other pin 22 to bend the shape memory portion 6 in the work portion 4 about 45 degrees. Then, the work portion 4 was rotated at 200 rpm while keeping this state of bending, and the time elapsed before the shape memory portion 6 fractured was measured.

As a result of the above fatigue fracture tests, the conventional samples were found to fracture in about 5 minutes on average, the first method samples were found to fracture in about 14 minutes on average, and the second method samples were found to fracture in about 11 minutes on average.

From the test results, it can be said that the reamer A of the present invention, having the shape memory portion 6 in the range of about 4 mm from the tip 3 of the work portion 4, has higher durability as compared to the reamer having the superelastic characteristic along the whole length.

As described above in detail, in the root canal treatment tool according to the present invention, by forming the shape memory portion having the shape memory characteristic in the range of a predetermined length range from the tip of the work portion, and the superelastic portion having the superelastic characteristic in a manner continuous with the shape memory portion, it is possible to make the shape memory portion exert flexibility and be easily deformed.

For this reason, at the time of starting the treatment of the root canal, by bending the shape memory portion in correspondence to the shape of the patient's root canal, it is possible to make the shape memory portion exert a function as a guide. Moreover, since the shape memory portion can be flexibly deformed in response to the action of external force, even if the tip of the work portion reaches the root sharp mouth, the shape memory portion does not cut the wall of the root canal more than required, and hence can be prevented from deviating from the root canal.

Further, since the shape memory portion has extremely high flexibility, the shape memory portion can exert high durability for repeated bends, and hence can elongate the time that elapses before it is brought into fatigue fracture, as compared to the root canal treatment tool having the superelastic characteristic along the whole length of the work portion.

Still further, according to the first manufacturing method and the second manufacturing method according to the present invention, a wire having a superelastic characteristic is previously subjected to a working of removing metal to be formed into the shape of an objective root canal treatment tool. Then, the tip portion of a work portion is again subjected to heat treatment, or a portion of the wire exerting the superelastic characteristic is again subjected to heat treatment, to exert a shape memory characteristic. Then, the portion having the shape memory characteristic, and the portion that is continuous with the portion having the shape memory characteristic and has the superelastic characteristic, are subjected to the working of removing metal. In this manner, the root canal treatment tool that has the work portion having the shape memory characteristic in the tip and the superelastic characteristic in the remaining portion can be manufactured.

Incidentally, although the heat treatment of the predetermined portion of the wire is performed by the above methods, it is not intended to limit the method of heat treatment. Rather, the work piece can be worked into a heat-treated portion and a non-heat-treated portion by various methods.

What is claimed is:

1. A root canal treatment tool that is formed in a shape of a rod and has a work portion formed in a predetermined length from a tip and a shank formed in a manner continuous with the work portion,
    wherein the work portion has a shape memory characteristic in a maximum length of about ¾ of the work portion, and a superelastic characteristic in a remaining portion.

2. The root canal treatment tool according to claim 1, wherein the root canal treatment tool is made of Ni—Ti alloy.